(12) United States Patent
Cummins et al.

(10) Patent No.: US 11,364,055 B2
(45) Date of Patent: Jun. 21, 2022

(54) OCCIPITAL PLATE AND HINGED ROD ASSEMBLY

(71) Applicant: Zavation, LLC, Flowood, MS (US)

(72) Inventors: John Franklin Cummins, Flowood, MS (US); Colbert Yeates Williams, Brandon, MS (US)

(73) Assignee: Zavation, LLC, Flowood, MS (US)

( * ) Notice: Subject to any disclaimer, the term of this patent is extended or adjusted under 35 U.S.C. 154(b) by 0 days.

(21) Appl. No.: 17/010,421

(22) Filed: Sep. 2, 2020

(65) Prior Publication Data
US 2022/0061893 A1 Mar. 3, 2022

(51) Int. Cl.
*A61B 17/70* (2006.01)

(52) U.S. Cl.
CPC ...... *A61B 17/7058* (2013.01); *A61B 17/7032* (2013.01)

(58) Field of Classification Search
CPC ............ A61B 17/80–8095; A61B 17/70–7098
See application file for complete search history.

(56) References Cited

U.S. PATENT DOCUMENTS

| | | | |
|---|---|---|---|
| 6,524,315 B1 | 2/2003 | Selvitelli et al. | |
| 6,547,790 B2 | 4/2003 | Harkey, III et al. | |
| 6,902,565 B2 | 6/2005 | Berger et al. | |
| 7,141,051 B2 | 11/2006 | Janowski et al. | |
| 7,232,441 B2 | 6/2007 | Altarac et al. | |
| 7,303,563 B2 | 12/2007 | Poyner et al. | |
| 7,517,359 B2 | 4/2009 | Drewry et al. | |
| 7,572,282 B2 | 8/2009 | Boomer et al. | |
| 7,575,588 B2 | 8/2009 | Barker et al. | |
| 7,618,443 B2 * | 11/2009 | Abdou ............... | A61B 17/6433 606/267 |
| 7,621,942 B2 | 11/2009 | Piehl | |
| 7,695,500 B2 | 4/2010 | Markworth | |
| 7,776,070 B2 | 8/2010 | Null et al. | |
| 7,901,433 B2 | 3/2011 | Forton et al. | |
| 7,909,852 B2 | 3/2011 | Boomer et al. | |
| 8,109,974 B2 | 2/2012 | Boomer et al. | |
| 8,147,519 B2 | 4/2012 | Wilcox | |
| 8,147,527 B2 | 4/2012 | Hoffman et al. | |
| 8,187,277 B2 | 5/2012 | Paul et al. | |
| 8,226,695 B2 | 7/2012 | Moore et al. | |
| 8,246,662 B2 | 8/2012 | Lemoine et al. | |

(Continued)

OTHER PUBLICATIONS

U.S. Appl. No. 61/239,309 (Zentko), filed Sep. 2, 2009 (incorporated by reference in U.S. Patent Application Publication No. 2012/0065686 and U.S. Pat. No. 9,877,747) (Year: 2009).*

*Primary Examiner* — Nicholas J Plionis
(74) *Attorney, Agent, or Firm* — IP & T Group LLP

(57) ABSTRACT

An occipital plate and hinged rod assembly. The occipital plate having a screw-attachment section having through holes for securing the occipital plate to a skull, a laterally-extending section, a tulip connector, a slide clip disposed underneath the laterally-extending section and engaging a base of the tulip connector, and an insert ring encompassing side walls of tulip connector. The laterally-extending section, the tulip connector, the slide clip, and the insert ring have respective surfaces with complementary curvatures that fit together. The hinged rod assembly is connected to the occipital plate by rods.

13 Claims, 15 Drawing Sheets

(56) References Cited

U.S. PATENT DOCUMENTS

| | | |
|---|---|---|
| 8,337,496 B2 | 12/2012 | Piehl |
| 8,348,981 B2 | 1/2013 | Cheema et al. |
| 8,394,131 B2 | 3/2013 | Wing et al. |
| 8,506,567 B2 | 8/2013 | Ziemek et al. |
| 8,556,942 B2 | 10/2013 | Ziolo et al. |
| 8,636,737 B2 | 1/2014 | Lemoine |
| 8,690,923 B2 | 4/2014 | Lynch |
| 8,728,080 B2 | 5/2014 | Boomer et al. |
| 8,740,953 B2 | 6/2014 | Hoffman et al. |
| 8,795,339 B2 | 8/2014 | Boomer et al. |
| 8,870,918 B2 | 10/2014 | Boomer et al. |
| 8,876,872 B2 | 11/2014 | Ziolo et al. |
| 8,894,695 B2 | 11/2014 | Moore et al. |
| 8,900,276 B2 | 12/2014 | Purcell et al. |
| 8,986,351 B2 | 3/2015 | Gephart et al. |
| 9,155,565 B2 | 10/2015 | Boomer et al. |
| 9,204,901 B2 | 12/2015 | Black et al. |
| 9,216,042 B2 | 12/2015 | Berrevoets et al. |
| 9,232,966 B2 | 1/2016 | Refai |
| 9,247,964 B1 | 2/2016 | Shoshtaev |
| 9,283,004 B2 | 3/2016 | Hammer et al. |
| 9,381,044 B2 | 7/2016 | Robinson et al. |
| 9,387,013 B1 | 7/2016 | Shoshtaev et al. |
| 9,439,687 B2 | 9/2016 | Lemoine |
| 9,486,248 B2 | 11/2016 | Gephart et al. |
| 9,486,249 B2 | 11/2016 | Hammer et al. |
| 9,498,258 B2 | 11/2016 | Boomer et al. |
| 9,526,528 B2 | 12/2016 | Sutterlin, III |
| 9,532,811 B2 | 1/2017 | Black et al. |
| 9,549,764 B2 | 1/2017 | Sutterlin, III |
| 9,566,094 B2 | 2/2017 | Black |
| 9,717,532 B2 | 8/2017 | Refai |
| 9,717,535 B2 | 8/2017 | Refai et al. |
| 9,757,162 B2 | 9/2017 | Purcell et al. |
| 9,770,269 B1 | 9/2017 | Shoshtaev |
| 9,877,747 B2 * | 1/2018 | Black ................ A61B 17/7055 |
| 9,956,009 B1 | 5/2018 | Shoshtaev |
| 9,974,572 B2 | 5/2018 | Boomer et al. |
| 9,993,271 B2 | 6/2018 | Hammer et al. |
| 10,022,160 B2 | 7/2018 | Robinson et al. |
| 10,064,661 B2 | 9/2018 | Berrevoets et al. |
| 10,136,925 B2 | 11/2018 | Shoshtaev |
| 10,265,108 B2 | 4/2019 | Pischl et al. |
| 10,368,918 B2 | 8/2019 | Shoshtaev et al. |
| 10,492,835 B2 | 12/2019 | Lee et al. |
| 10,507,044 B2 | 12/2019 | Black |
| 10,524,841 B2 | 1/2020 | Black et al. |
| 10,561,454 B2 | 2/2020 | Lee et al. |
| 10,588,668 B2 | 3/2020 | Refai et al. |
| 10,610,261 B2 | 4/2020 | Doose et al. |
| 10,617,450 B2 | 4/2020 | Black et al. |
| 10,653,451 B2 | 5/2020 | Refai |
| 10,695,104 B2 | 6/2020 | Berrevoets et al. |
| 10,722,275 B2 | 7/2020 | Boomer et al. |
| 2004/0153070 A1 | 8/2004 | Barker et al. |
| 2005/0288669 A1* | 12/2005 | Abdou ............... A61B 17/6433 606/246 |
| 2007/0118121 A1 | 5/2007 | Purcell et al. |
| 2007/0225711 A1 | 9/2007 | Ensign |
| 2007/0233119 A1 | 10/2007 | Markworth |
| 2008/0045955 A1 | 2/2008 | Berrevoets et al. |
| 2008/0051783 A1 | 2/2008 | Null et al. |
| 2008/0177313 A1* | 7/2008 | Lemoine ............ A61B 17/7055 606/250 |
| 2008/0177314 A1* | 7/2008 | Lemoine ............ A61B 17/8023 606/250 |
| 2010/0069960 A1* | 3/2010 | Chaput ............... A61B 17/7071 606/249 |
| 2010/0094351 A1* | 4/2010 | Haggenmaker .... A61B 17/7044 606/286 |
| 2010/0222779 A1* | 9/2010 | Ziemek ............... A61B 17/8042 606/71 |
| 2011/0190824 A1* | 8/2011 | Gephart ............. A61B 17/7059 606/278 |
| 2012/0065686 A1* | 3/2012 | Black ................. A61B 17/7044 606/252 |
| 2014/0324108 A1* | 10/2014 | Orbay ................ A61B 17/8004 606/289 |
| 2016/0143664 A1 | 5/2016 | Garcia et al. |
| 2018/0280063 A1 | 10/2018 | Lee et al. |
| 2018/0325562 A1 | 11/2018 | Robinson et al. |
| 2018/0344361 A1 | 12/2018 | Fiechter et al. |
| 2018/0353218 A1 | 12/2018 | Fiechter et al. |
| 2019/0008563 A1 | 1/2019 | Berrevoets et al. |
| 2019/0117274 A1 | 4/2019 | Purcell |
| 2019/0175227 A1 | 6/2019 | Shoshtaev |
| 2019/0314061 A1 | 10/2019 | Shoshtaev et al. |
| 2020/0060729 A1 | 2/2020 | Lee et al. |
| 2020/0078054 A1 | 3/2020 | Black |
| 2020/0121370 A1* | 4/2020 | Finn ................... A61B 17/7044 |
| 2020/0170695 A1 | 6/2020 | Lee et al. |
| 2020/0187990 A1 | 6/2020 | Doose et al. |
| 2020/0222084 A1 | 7/2020 | Refai et al. |

\* cited by examiner

OCCIPITAL PLATE AND HINGED ROD ASSEMBLY

BACKGROUND OF THE INVENTION

Field of the Invention

The present invention relates to implant devices for immobilizing vertebrae of the spinal column relative to the skull.

Description of the Related Art

In general, elongate members, such as spinal rods, have been mounted to the spinal column in order to stabilize or immobilize vertebrae of the spinal column for a variety of purposes. For instance, spinal rods are often secured to adjacent vertebral bodies via anchor members in order to promote fusion of the two vertebrae as a treatment for degenerative disc disease, spondylolisthesis, spinal stenosis, fractures of the vertebrae, and other conditions, as described in U.S. Pat. No. 9,216,042 (the entire contents of which are incorporated herein by reference).

When stabilizing portions of the spinal column, and in particular the cervical region of the spine, it is sometimes necessary to immobilize the skull in addition to vertebrae. The same type of elongate structures have been used to link and stabilize the vertebra, and in turn secured to the skull in order to keep the skull in an appropriate spatial relationship with respect to the spinal column (that is to immobilize vertebrae of the spinal column relative to the skull).

In many prior spinal stabilization procedures, elongate rods made of titanium or other materials were placed adjacent to the posterior side of the spine and anchored in place using screws connected to some type of coupling assembly. Examples of coupling assemblies for posterior fixation systems are described in U.S. Pat. No. 7,141,051; U.S. Published Application No. 2008/0045955; and U.S. Published Application No. 2007/0225711 (each of which has their entire contents incorporated herein by reference).

Previous systems for coupling spinal rods and other elongate stabilization devices to the skull vary. Prior systems typically utilized a plate mounted to the occipital region of the skull (that is an occipital plate) which was attached via a rod, a cable, a wire, a secondary plate, or attached to a region of the spine removed from the skull. In such spinal rod systems, two spinal rods were positioned generally parallel to the surface of the plate and then secured thereto by a bracket, yoke, or other receiving member, such as a U-shaped receiving member. The occipital plates were mounted to the skull with several screws disposed in screw holes of the plate. Since the base of the skull angles inward toward the spine, the plates mounted to the skull were not parallel to the posterior surfaces of the vertebrae, and the spinal rods (or the occipital plate at inflection zones) were bent to accommodate the angular difference. For instance, the bending of spinal rods to properly be received relative to an occipital plate is shown in U.S. Published Application No. 2004/0153070 (the entire contents of which are incorporated herein by reference). Yet, as described in the '042 patent noted above, the bending of the rod can fatigue the rod material, and makes it difficult to reposition the elements of the stabilization system. The 042 patent noted above used an articulated fixation device for securing an occipital plate member thereof to a skull and at least one spinal rod thereof to a vertebral bone. In one form, an adjustable bridge member was provided that was adjustably connected to both the plate member and the spinal rod. The adjustable connections included an upper and rearward pivot connection between the plate member and the bridge member and a lower and forward pivot connection between the spinal rod and the bridge member.

U.S. Pat. No. 9,526,528 the entire contents of which are incorporated herein by reference) describes occipital plates and assemblies combining occipital plates with one of several types of spinal rods or cervical plates in a procedure to fuse a portion of a skull to a portion of a spine including an occipital plate with mesh portions. The mesh portions could be used to augment the bone screws delivered via through holes in the occipital plate. The mesh portions could be sized so that the gaps in the mesh were bigger than the outer diameter of the bone screw but smaller than the head of the screw so that bone screws could be delivered through the mesh to bind the mesh to the skull. In another embodiment, the '528 patent utilized a unitary occipital plate having an occipital bony attachment section with an array of through holes for securing the unitary occipital plate to a portion of a skull, and at least one connector section, caudal to an inflection zone that separates the occipital bony attachment section from the connector section. In this embodiment, each connector section had at least one threaded element to connect the unitary occipital plate to a cervical plate for connection with a spine, and the occipital bony attachment section included at least one mesh portion distinct from the array of through holes passing through the unitary occipital plate; the mesh portion for receipt of bone screws to allow a distal end of the bone screw to pass through the mesh portion and enter the skull while capturing a proximal end of the bone screw so that the bone screw pulls the mesh portion towards the skull.

U.S. Pat. No. 6,902,565 (the entire contents of which are incorporated herein by reference) describes a plate designed to be mounted to the occipital region of the skull by a plurality of short expansion head screws. The plate receives a pair of rods that may be further mounted to one or more vertebrae. In many cases these rods are pre-bent so that the majority of the rods may be positioned parallel to the spine, with the ends bent transversely in order to be secured to the plate by a clamp plate or bracket. Some embodiments include plates that are bent in order to receive the rods that are parallel to the spine.

U.S. Published Application No. 2008/0051783 (the entire contents of which are incorporated herein by reference) describes a plate device having a pair of u-shaped rod receiving members that protrude from lateral wings of the plate. The wings may be shifted laterally and medially, and the rod receiving members may rotate to adjust the direction in which a connecting member (such as a spinal rod) is received. The spinal rods must be positioned so that they are generally parallel to the plate surface in order to fit into the rod receiving members. Therefore, the ends of the rod must be bent away from the axis of the spine, which is not parallel to the plate surface, and into the u-shaped channels of the receiving members.

U.S. Pat. No. 6,524,315 (the entire contents of which are incorporated herein by reference) describes a plate secured to the bone by a plurality of screws. The plate is fitted with slotted bolts designed for receiving a rod or cable. The base of the slotted bolt is recessed in the plate at its base. A support platform may be fitted over the bolt to help hold the rod or cable. A nut fastens over the threaded end of the slotted bolt to trap the rod or cable within the bolt, securing it to the plate. The bolt may be rotated to adjust the direction of the rod or cable.

U.S. Published Application 2007/0233119 (the entire contents of which are incorporated herein by reference) describes a plate device with polyaxial connector head assemblies including a connector body that receives a spinal rod and a connector head pivotably connected to the connector body and configured to be secured to the plate so that the connector assemblies provide limited polyaxial movement of the spinal rods with respect to the plate. However, the coupling heads are relatively bulky and still hold the spinal rods relatively parallel to the plate surface.

In U.S. Published Application 2007/0118121 (the entire contents of which are incorporated herein by reference), a fixation plate includes a laterally extending arm coupled to a pair of spinal rods by sliding links that are able to slide along and pivot about the arms. However, ends of the spinal rods are held relatively close to the fixation plate, and positioning of the sliding links is limited to sliding and pivoting along the fixed laterally extending arms. Further, the sliding links are locked in place by clamping together top and bottom portions thereof with a set screw positioned at a distance from the laterally extending arm, which compresses a rounded portion of the link about the arm in order to inhibit sliding. However, the locking force between the sliding links and the laterally extending arms may not be able to prevent pivoting or sliding of the spinal rods relative to the fixation plate when sufficient force is applied.

U.S. Pat. No. 7,901,433 (the entire contents of which are incorporated herein by reference) describes an adjustable occipital plate system that permits spinal rods to be positioned at various angles with respect to the plane of the occipital plate. The horseshoe-shaped plate has a lateral arm extending from each side, with a variable connector securing each spinal rod to a lateral arm of the plate system. A gap separates the two lateral arms, and may allow some twisting of the plate arms and spinal rods. In addition, the horseshoe-shape of the plate may not allow all of the bone screws to be driven into the thickest and hardest bone which is typically in the central area of the occipital region of the skull. The horseshoe-plate of the '433 patent also will have to be bent because of its substantially flat configuration and the non-flat or curved configuration of the skull's occipital region. Bending of the relatively narrow, curved arms of the plate will undesirably further weaken the plate. Additionally, bending the plate and the rods involves trial-and-error and, as such, is typically a very time consuming process. This is particularly challenging with these types of occipital plate and spinal rod assembles where during surgery, the patient's occiput and cervical vertebrae are typically oriented one way relative to each other with the patient supported on an operating table, and need to be oriented another way relative to each other for final fixation of the assembly to the occiput and the cervical vertebrae. The connectors of the '433 patent hold the spinal rods below or even with the lateral arms, and thus relatively close to the spine. However, this can create interference with the cervical vertebrae immediately below the occiput (i.e., the C1 and C2 vertebrae), and potentially the brain stem where it may be exposed due to damage to surrounding bone.

U.S. Pat. No. 8,147,527 (the entire contents of which are incorporated herein by reference) describes an occipital plate for use in an occipito-cervico-thoracic (OCT) construct which was mounted to a patient's occipital bone. The occipital plate included an elongate central section aligned with a midline of the base and a pair of angled sections that project away from the central section and include attachment assemblies for securing a rod to the occipital plate. At least a portion of the attachment assemblies was rotatable with respect to the base so that the rods could be coupled to the occipital plate at a variety of angles with respect to the midline. The angular adjustability potentially could accommodate any misalignments in the rods. Additionally, the position of the attachment assemblies relative to the midline of the occipital plate was adjustable to thereby provide for medial-lateral adjustability when attaching the rods to the occipital plate as part of the OCT construct U.S. Pat. No. 7,909,852 (the entire contents of which are incorporated herein by reference) describes a spinal fixation device having first and second elongate members that are angularly adjustable relative to one another. Each elongate member can include a connecting feature formed on a terminal end thereof, and each connecting feature can be coupled to one another to allow angular movement of the first and second elongate members. The device can also include a locking mechanism that is adapted to couple to the connecting feature on each of the first and second elongate members to lock the elongate members in a fixed position relative to one another.

U.S. Pat. No. 10,588,668 (the entire contents of which are incorporated herein by reference) describes an articulating assembly includes a first elongated element for attachment to a first anatomical region, and a second elongated element for attachment to a second anatomical region. In at least one embodiment, a coupling connects the first and second elongated elements. The coupling includes a moveable joint configured to allow polyaxial movement of the first elongated element with respect to the second elongated element. The assembly further includes a locking mechanism. The locking mechanism is operable in an unlocked condition to permit polyaxial movement of the first elongated element with respect to the second elongated element, and a locked condition to immobilize the movable joint and fix the position of the first elongated element with respect to the second elongated element.

U.S. Pat. No. 10,561,454 (the entire contents of which are incorporated herein by reference) describes an articulating implant connector having a first body that defines a first rod-receiving recess, a second body that defines a second rod-receiving recess, a hinge pin rotatable relative to both of the first and second bodies and that couples the first body to the second body. The connector had a fastener configured to urge the first and second bodies towards one another along the rotation axis and thereby lock relative rotation of the first and second bodies about the rotation axis.

U.S. Pat. No. 8,147,519 (the entire contents of which are incorporated herein by reference) describes a spinal rod connector is that allows end-to-end connection of at least two spinal rods. The connector via an intermediate hinge allows for angular adjustment associated with a patient's anatomy. A locking mechanism could be used to fix a determined angle of the connector dependent upon the anatomy of the patient.

SUMMARY OF THE INVENTION

In one embodiment, there is provided an occipital plate having a screw-attachment section for securing with bone screw the occipital plate to a skull, a laterally-extending section connected to the screw-attachment section having at least one slot extending in a lateral direction, a tulip connector disposed in the at least one slot and comprising side walls which extend above the laterally-extending section, a slide clip disposed underneath the laterally-extending section and engaging a base of the tulip connector, and an insert ring encompassing the side walls of tulip connector. The laterally-extending section, the tulip connector, the slide clip, and the insert ring have respective surfaces with complementary curvatures that fit together.

In one embodiment, there is provided a hinged rod assembly having a female-type adapter having a housing integrally connected to a first rod, a male-type adapter integrally connected to a second rod, a pin inserted through a) a pair of aligned holes in the housing of the female-type adapter and b) through a hole in a cylindrical end of the male-type adapter, and a set screw which screws into female threads in the housing of the female-type adapter and binds the cylindrical end of the male-type adapter from rotation.

In one embodiment, there is provided an occipital plate and hinged rod assembly having the occipital plate described above, the hinged rod assembly described above, a pair of occipital plate rods extending from the occipital plate to the hinged rod assembly, and a pair of spine attachment rods extending from the hinged rod assembly away from the occipital plate.

It is to be understood that both the foregoing general description of the invention and the following detailed description are exemplary, but are not restrictive of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE INVENTION

The prior occipital plate and angle-adjusting rod assemblies noted above have complex mechanisms for attachment of the rods to the occipital plate and for adjustment of the relative angle of the rods to the spinal column and the relative angle of the rods to themselves.

Figure 1:
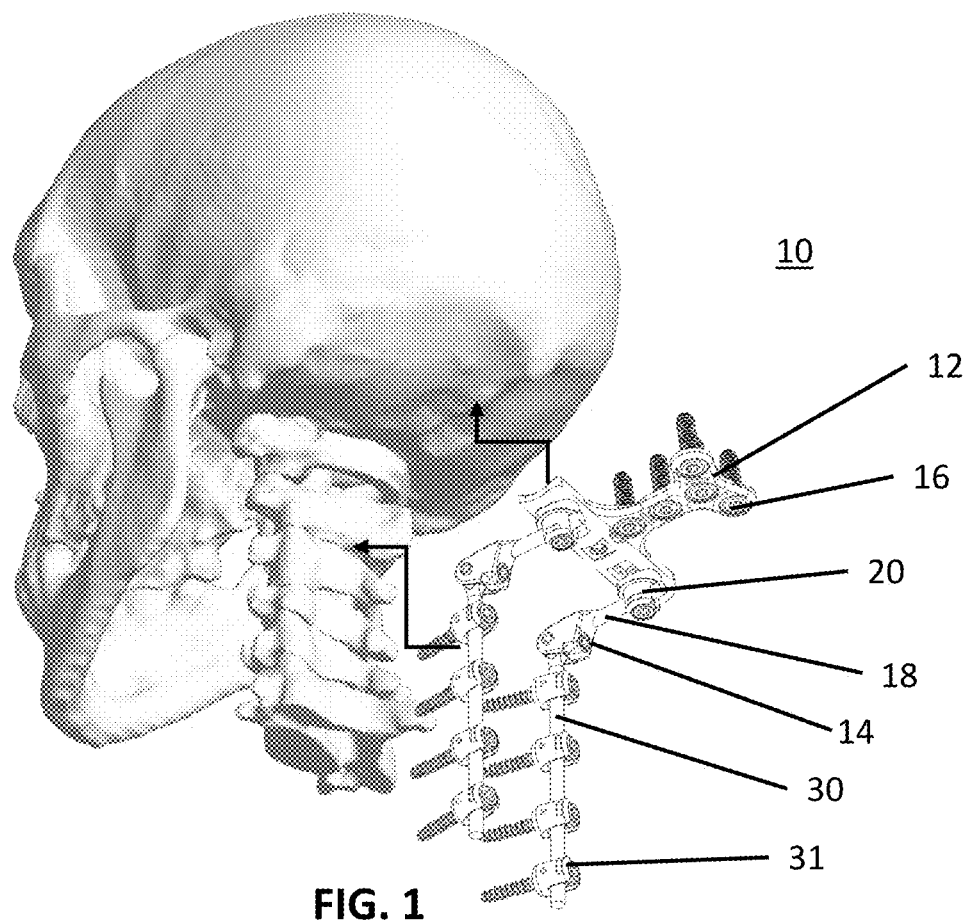
FIG. 1 is a depiction of one example of an occipital plate and hinged rod assembly of the present invention.
Figure 2:
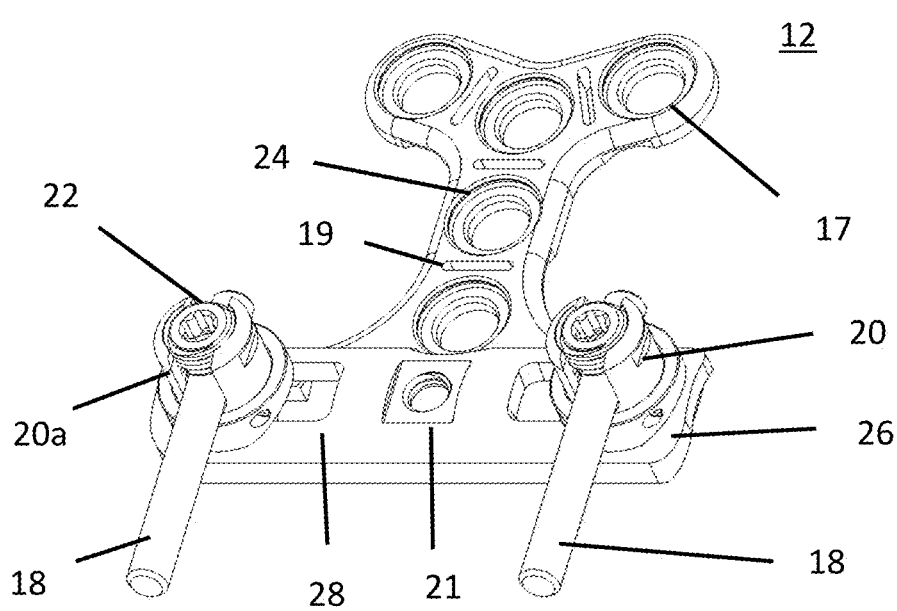
FIG. 2 is a depiction of the occipital plate of FIG. 1 showing a tulip post securing a rod thereto.

Shown below in FIG. 1 is a composite view of the inventive occipital plate and hinged rod assembly implant 10 as it would be attached to the skull and vertebra of a patient. The following descriptions describes components and aspects of the invention but do not limit the invention to those particular descriptions. As shown in FIGS. 1 and 2, the occipital plate and hinged rod assembly implant 10 has an occipital plate 12 and a hinged rod assembly 14. The plate 12 is attached to the base of the skull by bone screws 16 extending through screw holes 17 in the plate 12. The plate 12 is attached to rods 18 extending from the plate 12 to the hinged rod assembly 14. Each rod 18 as shown in FIG. 2 is attached to the plate 12 by having each rod 18 rest in a tulip post (or tulip connector) 20 having for example female threads on an interior sidewall thereof 20a and having set screw 22 (or other fastening mechanism) to secure the rod to the tulip post 20.

As shown in FIG. 2, the occipital plate 12 includes a screw-hole attachment section 24 and a laterally extending section 26 including a slot 28. As detailed below, the tulip post 20 can translate in the slot 28 before being secured and fixed to the tulip post 20, When fixed to the tulip post 20, rods 18 are fixed in lateral and rotational position and connect to the hinged rod assembly 14. As shown in FIG. 2, the occipital plate 12 can have cross-wise apertures 19 arranged nearby screw holes 17. The cross-wise apertures 19 permit the occipital plate 12 to be shaped to better conform to the shape of the skull (or other bone structure) that plate 12 will attach to). As shown in FIG. 2, the laterally-extending section 26 of the occipital plate 12 can have a threaded hole 21 for attachment of an insertion tool (not shown) to assist the doctor in placemen and positioning of the occipital plate 12

Figure 3:
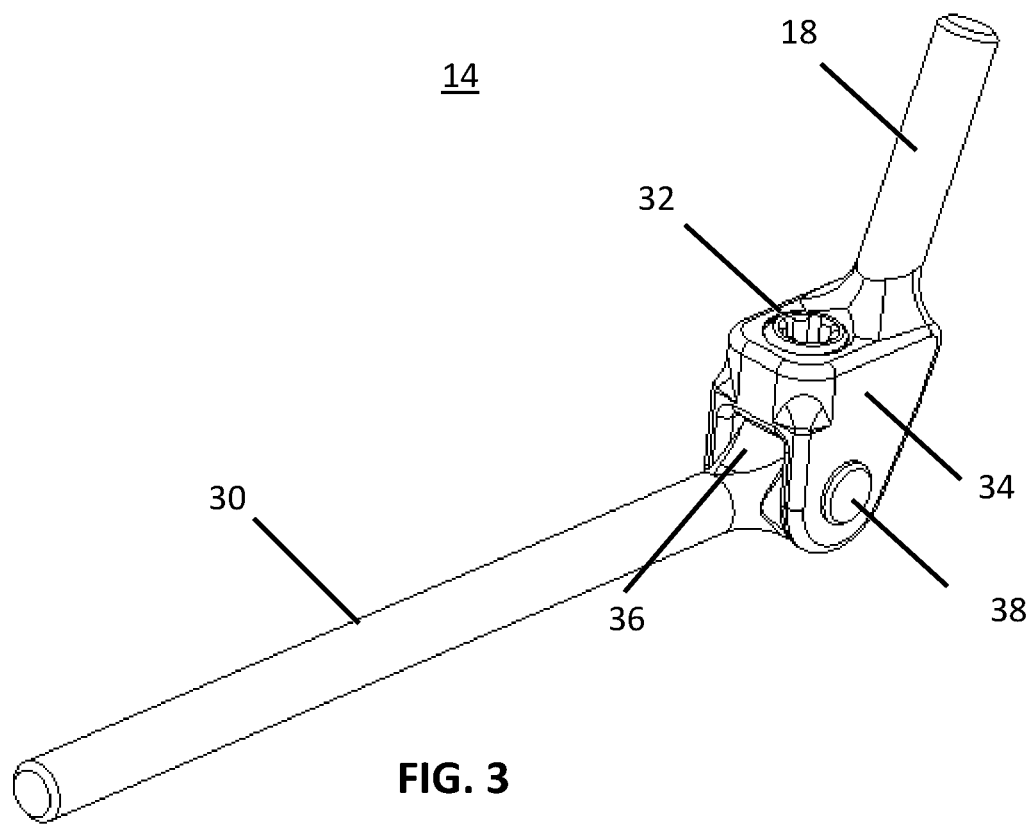
FIG. 3 is a depiction of the hinged rod assembly of FIG. 1
Figure 4:
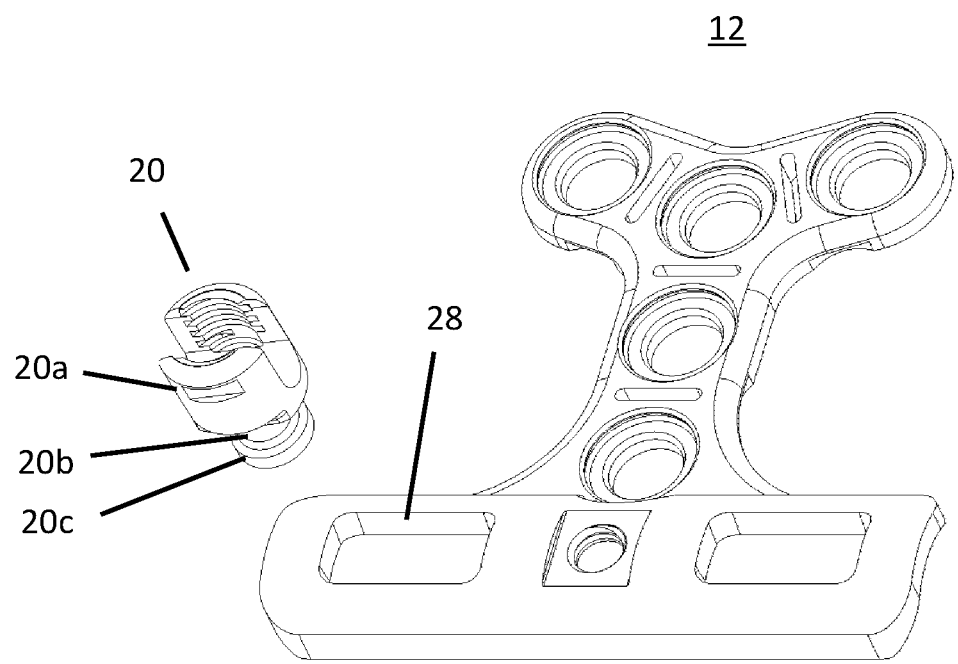
FIG. 4 is a depiction of the occipital plate of FIG. 1 showing assembly of the tulip post.

As shown in greater detail in FIG. 3, the hinged rod assembly 14 connects rod 18 to rod 30 which typically extends along and is secured to different vertebra by saddle member fixtures 31 (shown in FIG. 1) that secure rod 30 to the vertebra for example by bone screws similar to bone screws 16 used to secure the occipital plate 12 to the skull. More details of the hinged rod assembly 14 are given below, but as shown in FIG. 3, set screw 32 screws into housing 34 connected integrally with rod 18. The set screw 32 contacts a cylindrical end 36 of rod 30 and prevents rotation of the cylindrical end 36 about the pivot pin 38.

Figure 5:
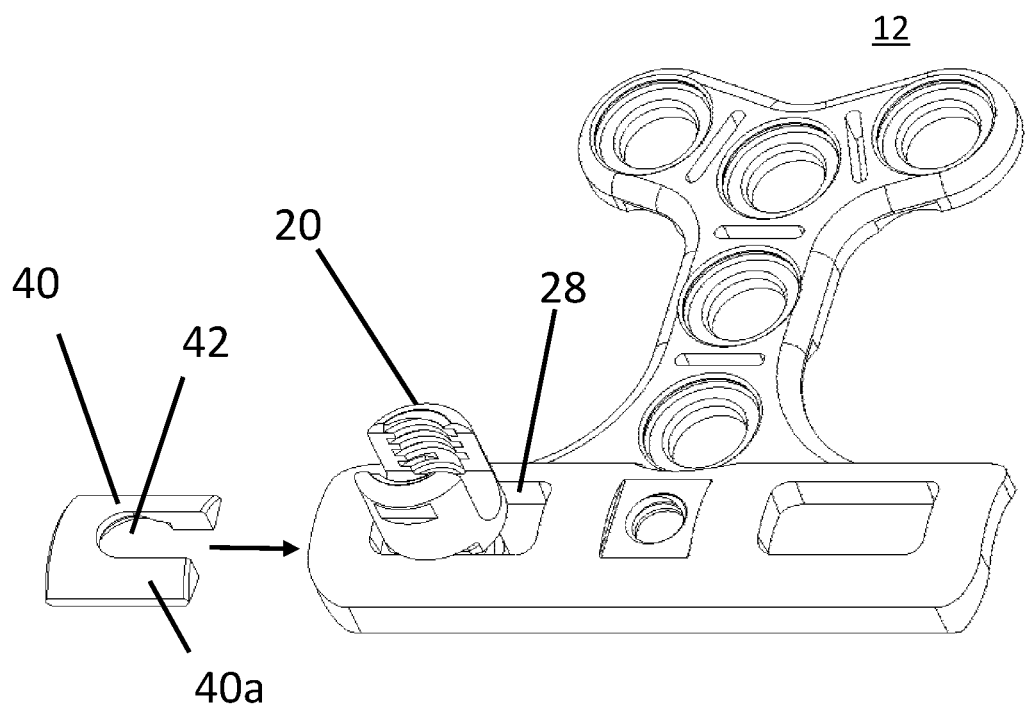
FIG. 5 is a depiction of the occipital plate of FIG. 1 showing further assembly of the tulip post.
Figure 6:
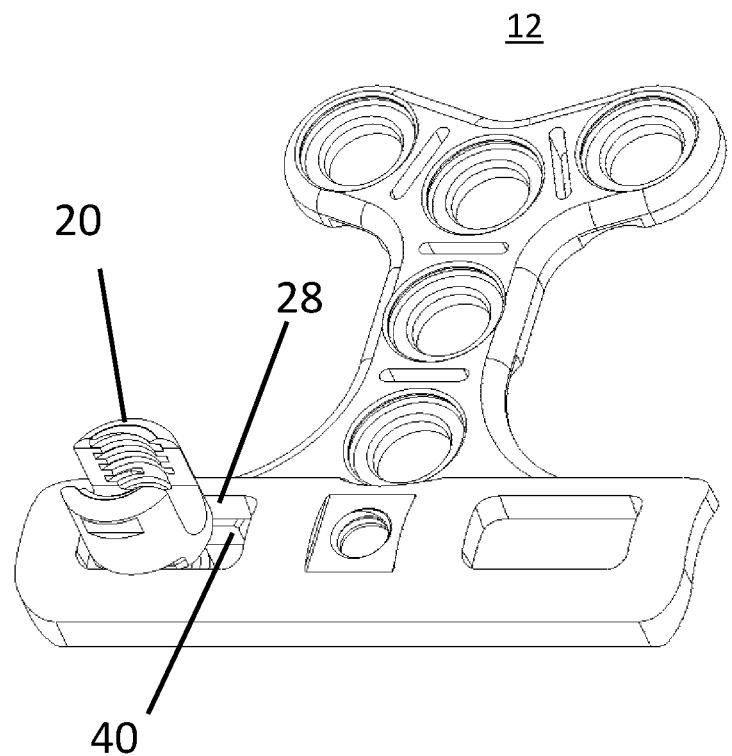
FIG. 6 is a depiction of the occipital plate of FIG. 1 showing further assembly of the tulip post.

As shown in assembly steps depicted in FIGS. 4-10, the tulip post 20 is insertable into the laterally extending slot 28 in the occipital plate 12 to accommodate different lateral spacings between the rods. A slide clip 40 containing a pocket 42 is inserted into groove 20b in tulip post by inserting the slide clip 40 between the underside of the plate 12 and a bottom retainer 20c of the tulip post 20 to secure the tulip post 20 in the laterally extending slot while maintaining (at this step) rotational capability of the tulip post 20. As shown in FIG. 5, slide clip 40 has a curved or contoured upper surface 40a that complements the curvature or contour of the underside of the plate 12. As shown in FIG. 6, the slide clip 40 is pushed until its pocket 42 is engaged in groove 20b of the tulip post 20. Note that a thickness of slide clip 42 is thinner near the pocket 42 so that once the slide clip is engaged in groove 20b, it will not readily disengage.

Figure 7:
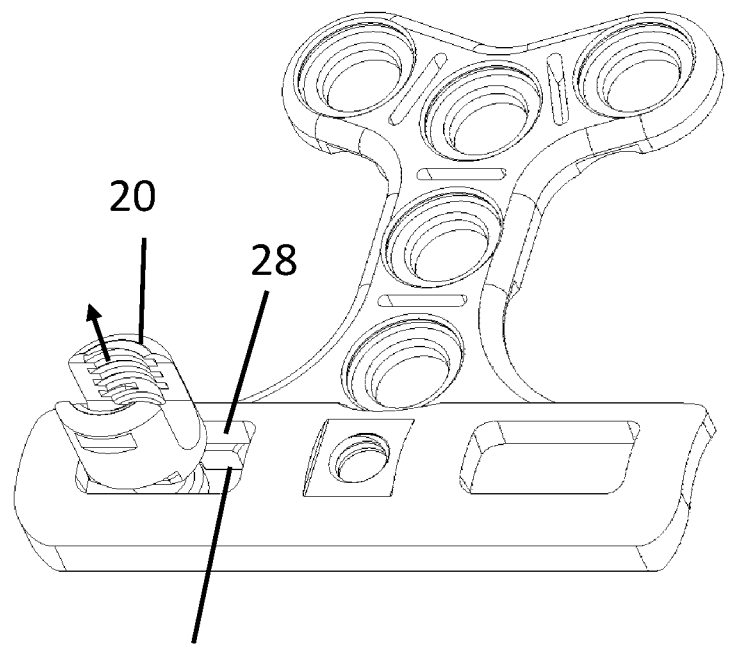
FIG. 7 is a depiction of the occipital plate of FIG. 1 showing further assembly of the tulip post.
Figure 8:
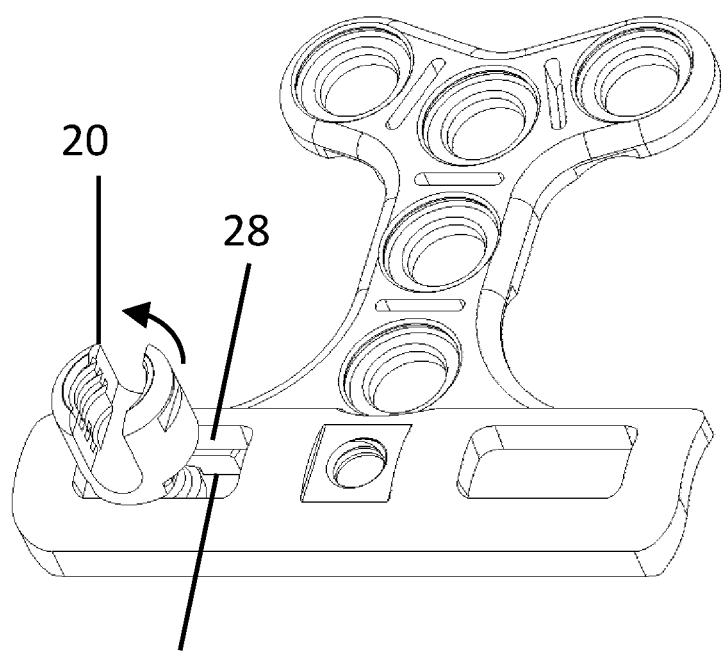
FIG. 8 is a depiction of the occipital plate of FIG. 1 showing further assembly of the tulip post.
Figure 9:
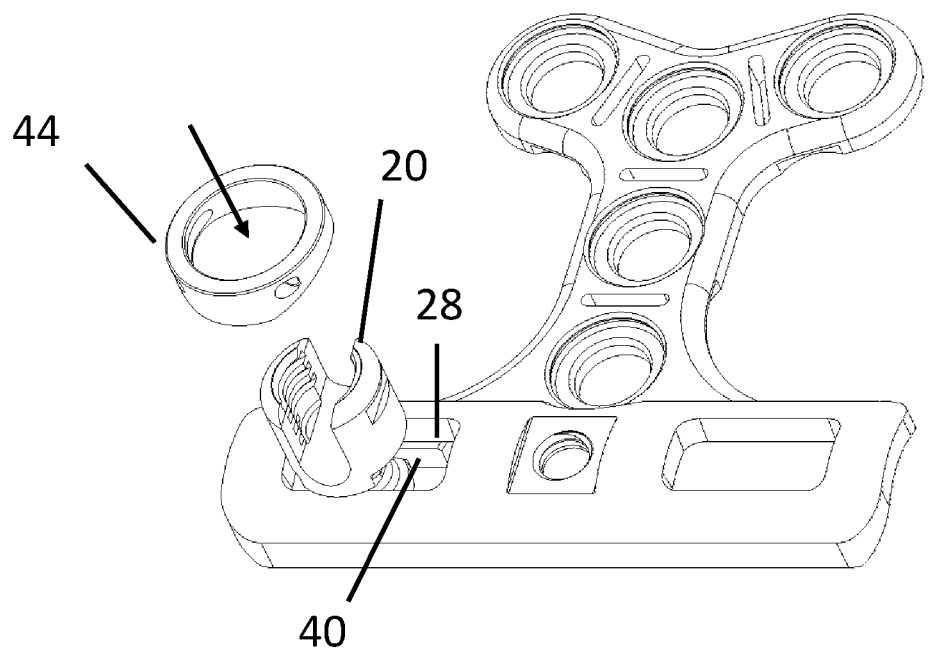
FIG. 9 is a depiction of the occipital plate of FIG. 1 showing further assembly of the tulip post.
Figure 10:
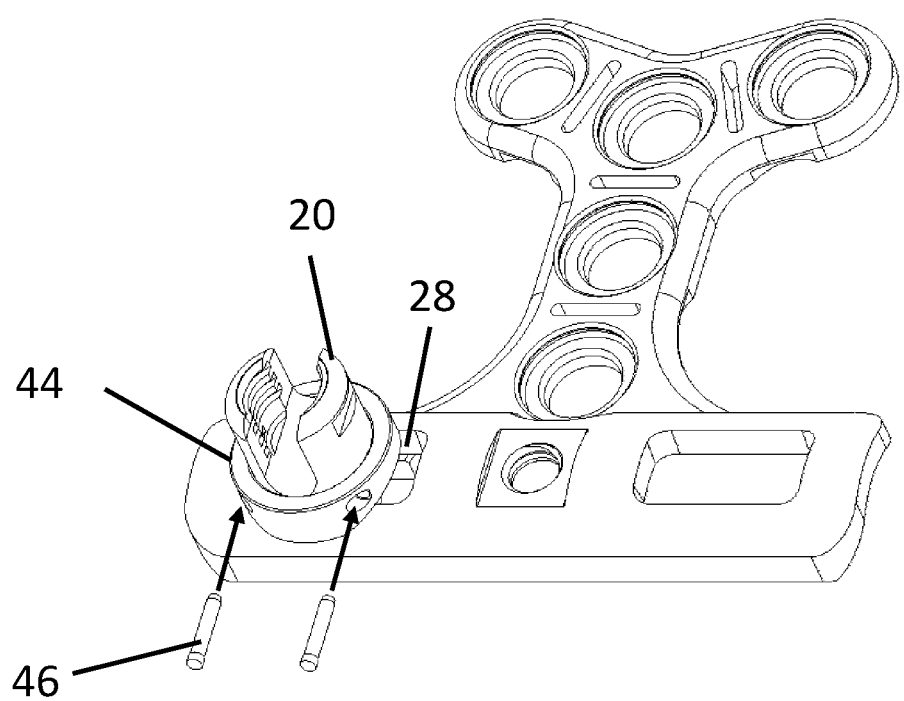
FIG. 10 is a depiction of the occipital plate of FIG. 1 showing further assembly of the tulip post.

The tulip post 20 can now be pulled upward until the bottom retainer 20c of the tulip post 20 is engaged in the slide clip pocket 42, as shown in FIG. 7. Afterwards, an insert ring 44 is slipped around the tulip post's sidewalls with pins 46 inserted into the insert ring 44 to secure the tulip post 20 to the plate 12 with a limited range of rotation. At this point in the assembly, the tulip post 20 can still be displaced laterally along the plate's laterally extending slot 28.

Figure 11:
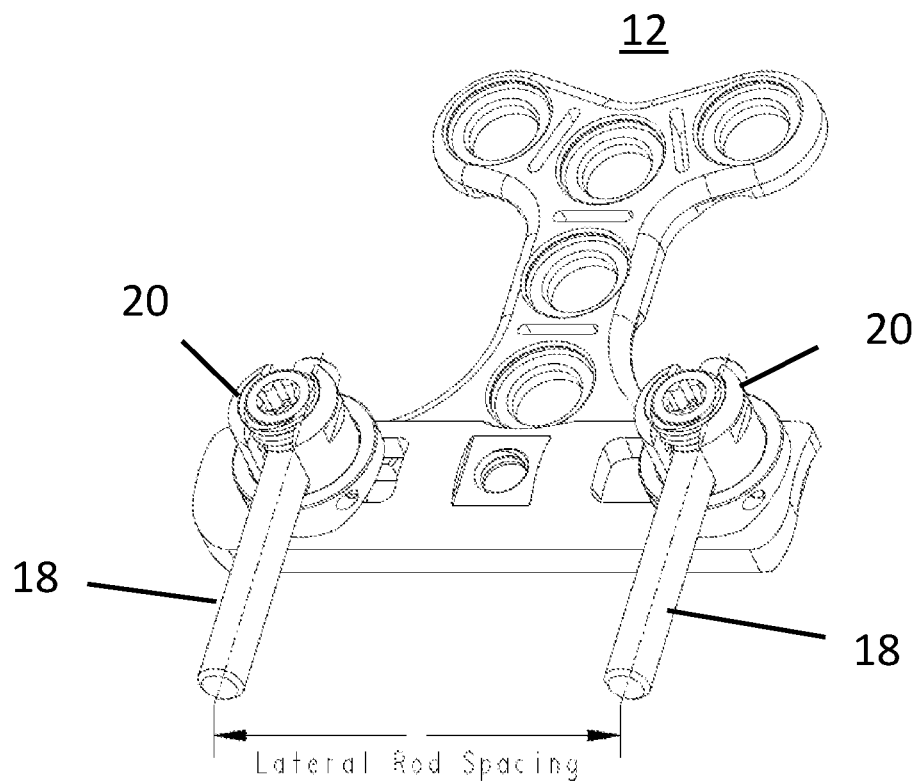
FIG. 11 is a depiction of one embodiment of the occipital plate of the present invention showing the lateral spacing adjustment capability.
Figure 12:
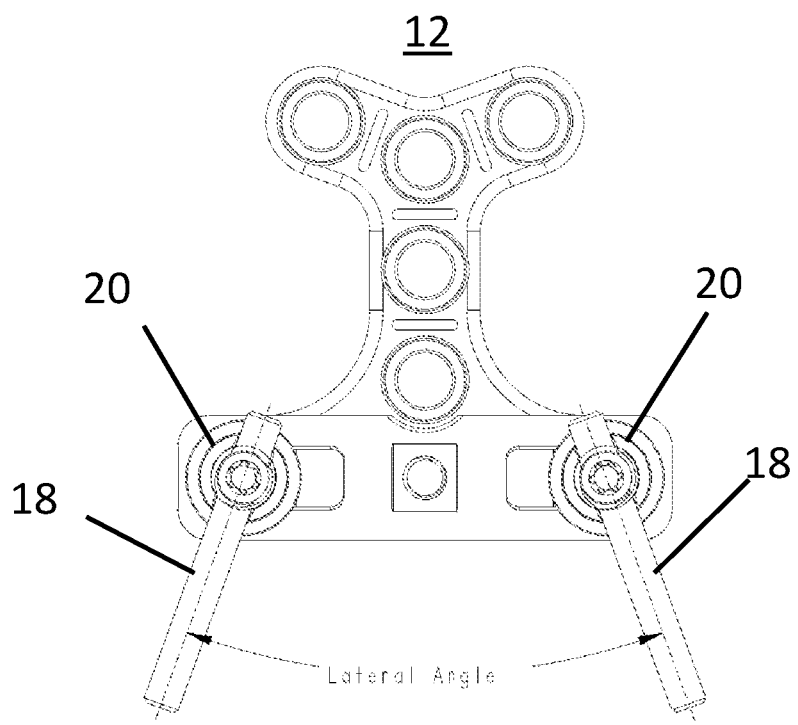
FIG. 12 is a depiction of another embodiment of the occipital plate of the present invention showing the lateral angle adjustment capability.
Figure 13:
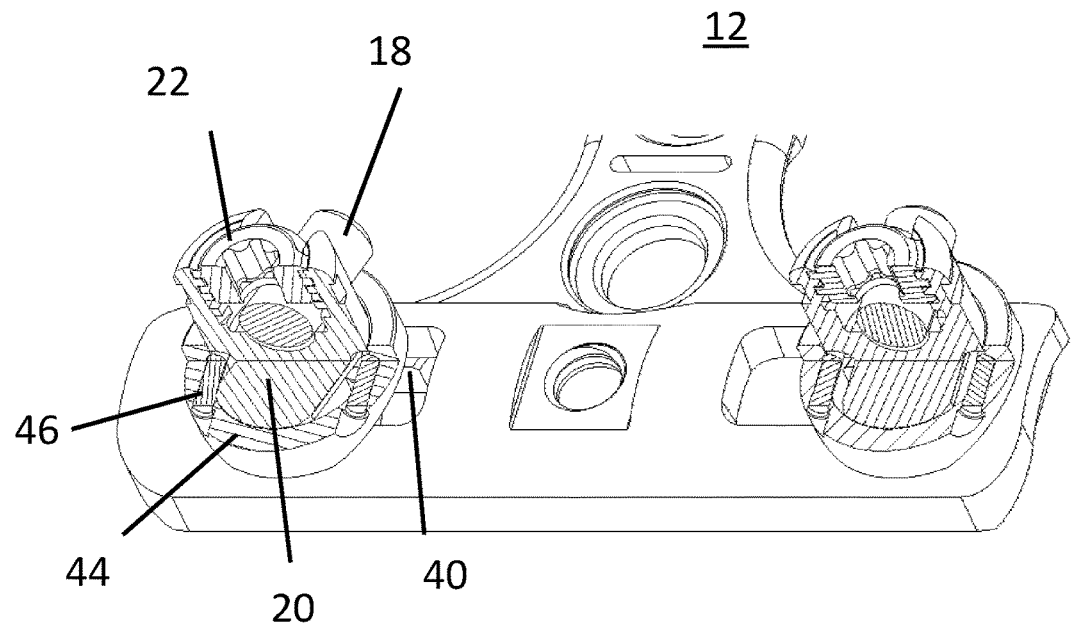
FIG. 13 is a depiction of another embodiment of the occipital plate of the present invention showing components for constraint of the angular adjustment shown in FIG. 12.
Figure 14A:
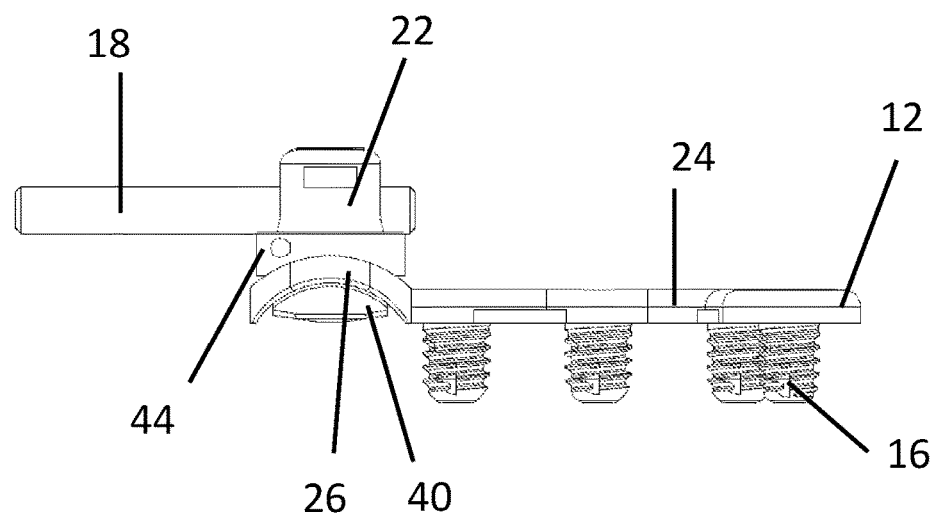
FIG. 14A is a depiction of the occipital plate of FIG. 1 showing respective surfaces having complementary curvatures that fit together on a laterally-extending section.
Figure 14B:
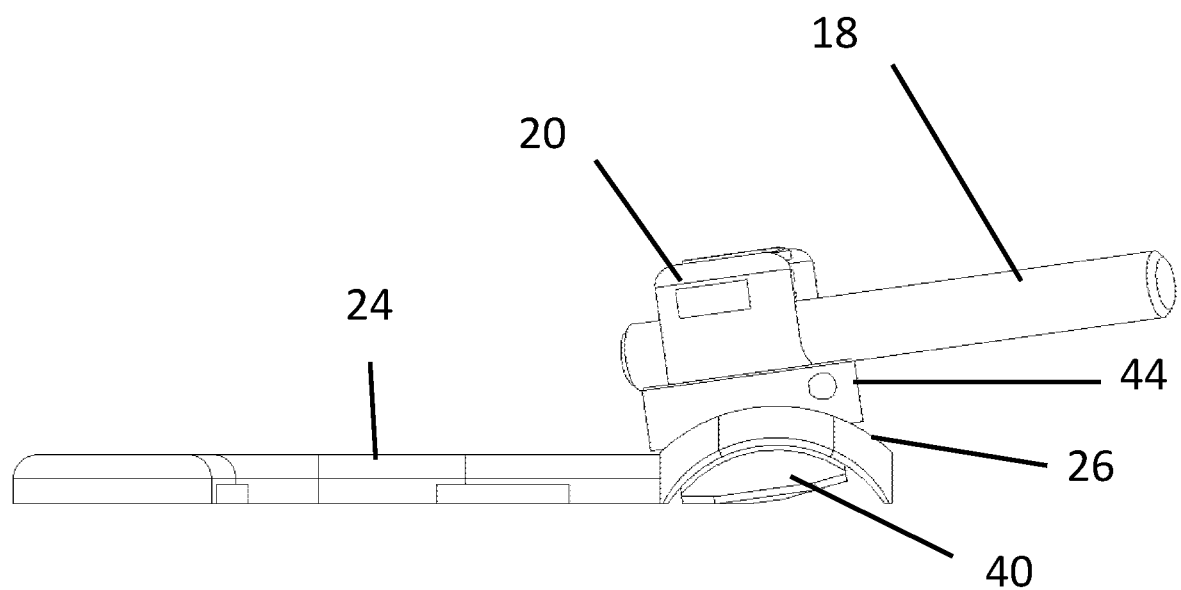
FIG. 14B is a depiction of the occipital plate of FIG. 1 showing rotation along the complementary curvatures shown in FIG. 14A.

FIGS. 11 and 12 are depictions of the occipital plate 12 showing the lateral displacement and angular positional capability of the present invention permitting rods 18 to be independently set to different lateral spacings and with different lateral angles. FIG. 13 is a depiction of the occipital plate 12 showing details of how pins 46 allow only limited rotation of rods 18 until screw 22 locks the assembly together as shown in FIGS. 14A and 14B. FIG. 14A illustrates that both the top surface of the extending flange section 26 and the underside of the insert ring 44 have complementing curvatures such that once in contact the insert ring may no longer rotate. FIG. 14B illustrates that, before the tulip post 20 is fixed to the laterally-extending section 26, it is rotatable about the longitudinal axis of the laterally-extending section 26.

Figure 15:
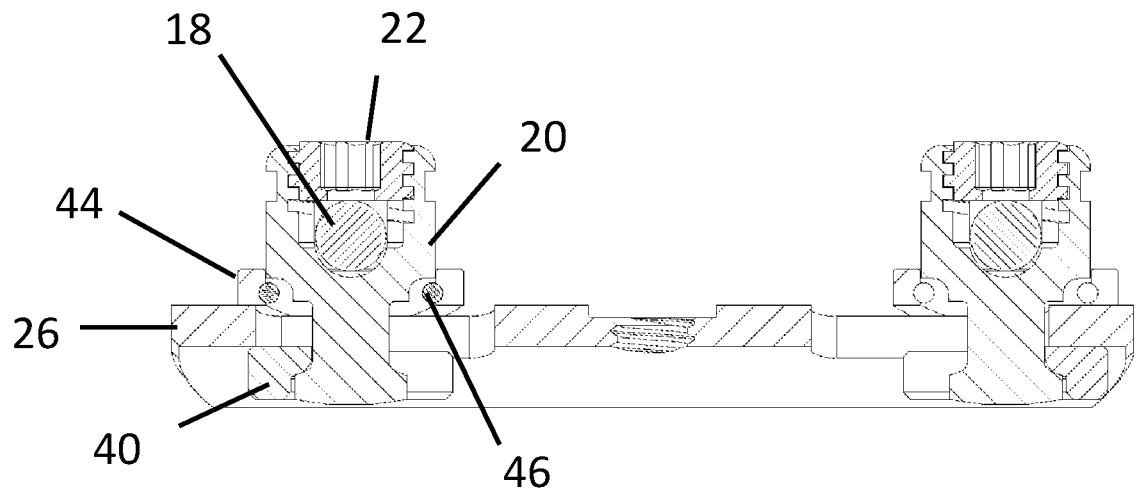
FIG. 15 is a depiction of the occipital plate of FIG. 1 in a locked configuration.

Once set screw 22 is tightened onto rod 18, in turn pushing rod 18 onto the insert ring 44, then the tulip post 20 is fixed to occipital plate 12 with no rotational or translational motion. FIG. 15 shows further details of the locked assembly with rod 18 under compression from screw 22. Rod 18 (in contact with insert ring 44 as seen in FIGS. 14A and 14B) itself then pushes downward on the insert ring 44 onto the top surface of the extending flange section 26 of the occipital plate 12 and thereby compressing the assembly of the tulip post 20, the slide clip 40, the laterally-extending section 26, and insert ring 44 together.

Figure 16:
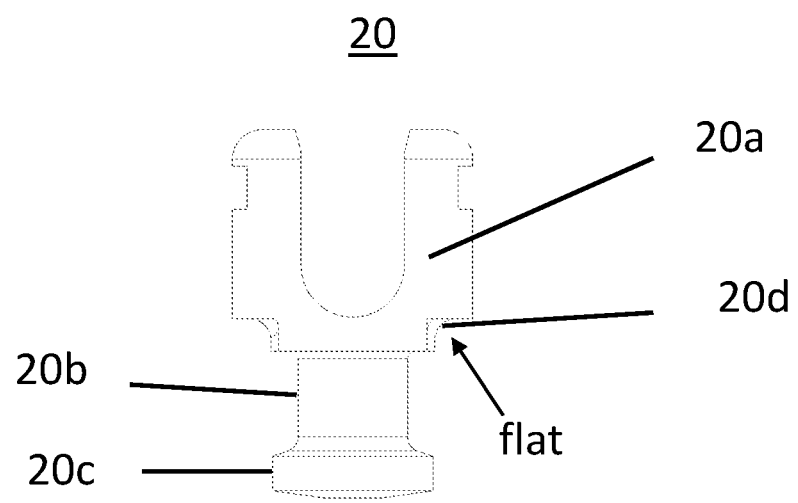
FIG. 16 is a depiction of the tulip post shown in FIG. 1.
Figure 17:
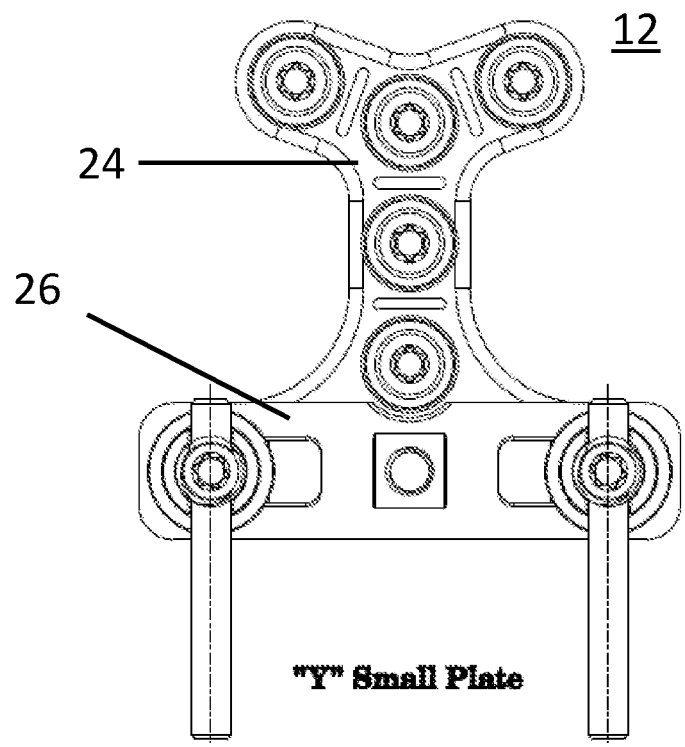
FIG. 17 is a depiction of another embodiment of the occipital plate of the present invention.
Figure 18:
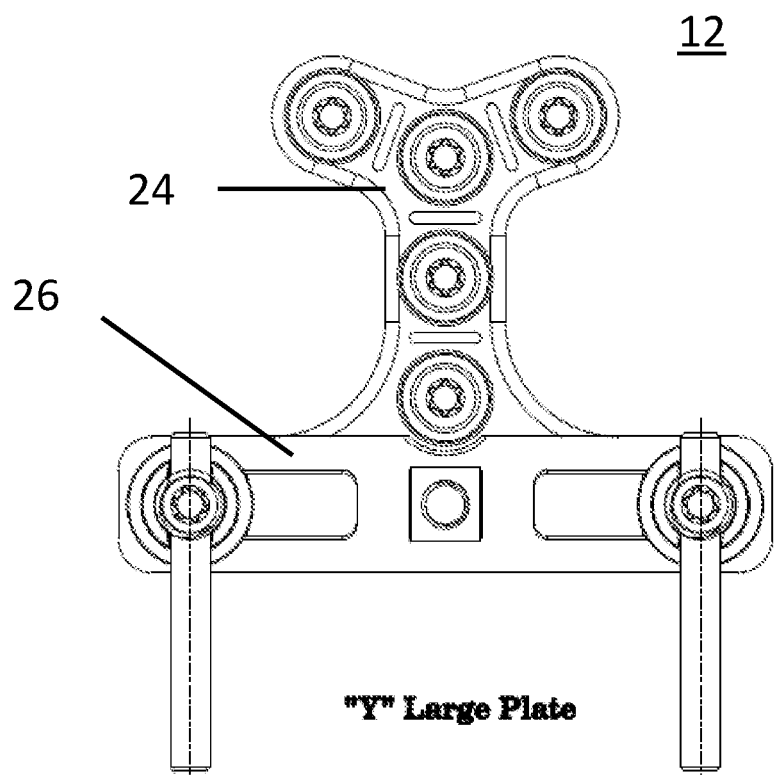
FIG. 18 is a depiction of another embodiment of the occipital plate of the present invention.
Figure 19:
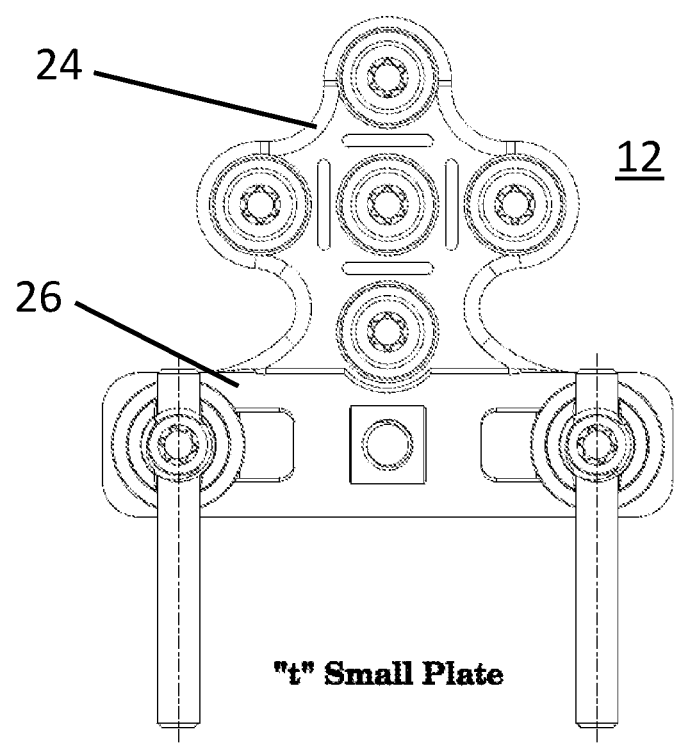
FIG. 19 is a depiction of another embodiment of the occipital plate of the present invention.
Figure 20:
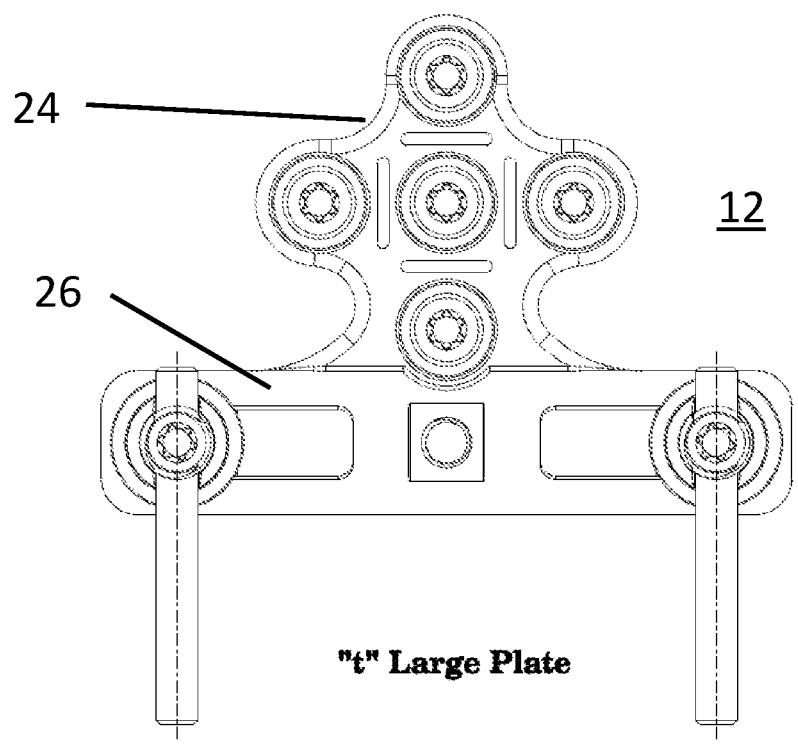
FIG. 20 is a depiction of another embodiment of the occipital plate of the present invention.
Figure 21:
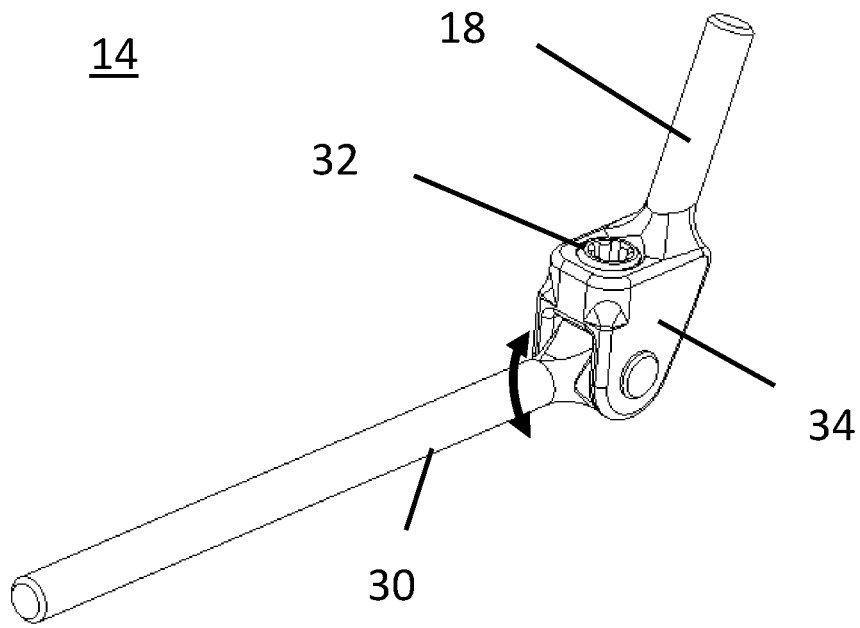
FIG. 21 is a depiction of the hinged plate assembly shown in FIG. 3 showing a direction of angular rotation of a spinal-extending rod.
Figure 22:
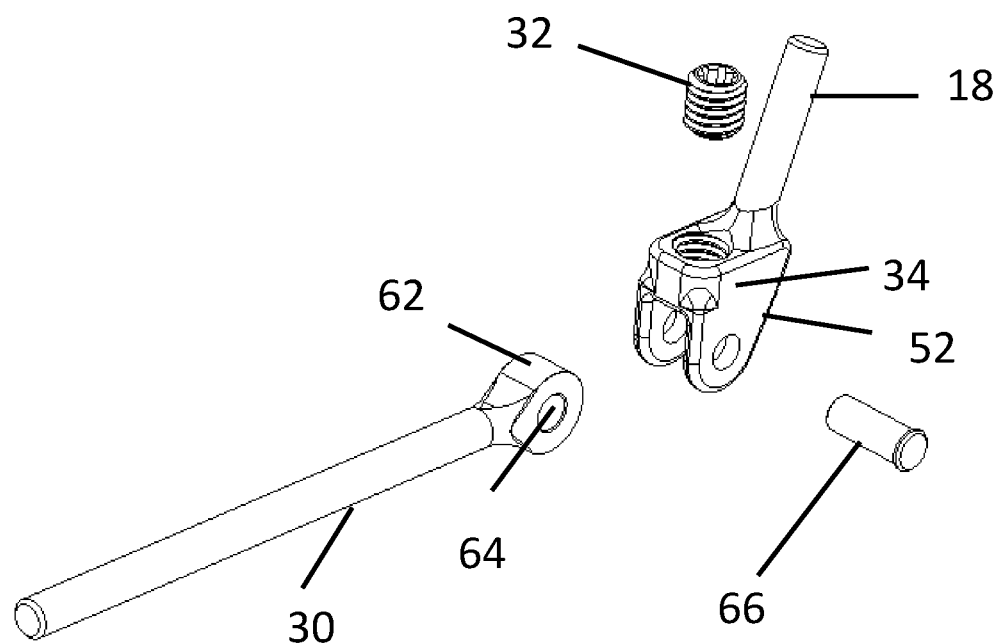
FIG. 22 is a depiction of the hinged plate assembly shown in FIG. 3 in an assembly format.

As shown in FIG. 16, the tulip post 20 has a flat 20d on a sidewall section underneath the sidewall 20a and above the groove 20b. The flat 20d of the tulip post is constrained from full rotation by contact with pins 46 in the insert ring 44 (prior to locking), and after locking the fixation of the insert ring 44 to the top surface of the extending flange section 26 (both having complementing curvatures as shown in FIG. 14) and the fixation of the insert ring 44 to rod 18 prevents subsequent rotation of rod 18.

FIGS. 17-20 are depictions of different occipital plates in which the shapes of the screw-attachment sections 24 are in the shape of a "Y" or a "t" for attachment to the skull. The laterally extending sections 26 have slots and use the same tulip connectors, slide clips, and insert rings (described above) to secure the rods to the occipital plates 12.

Figure 23:
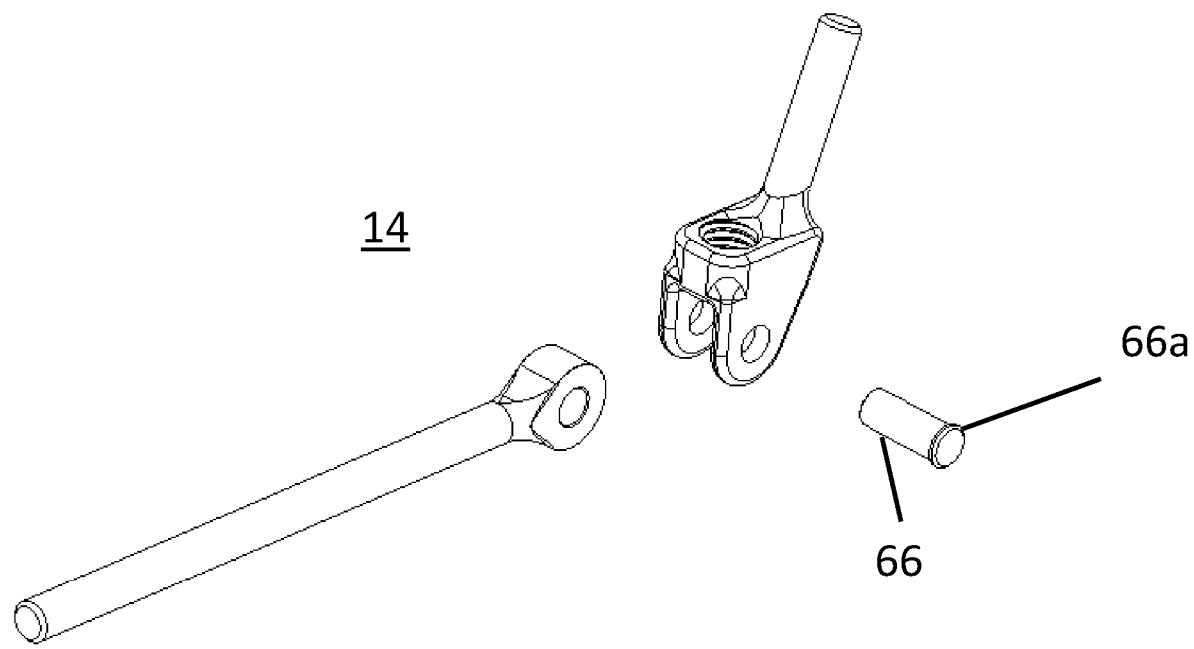
FIG. 23 is a depiction of the hinged plate assembly showing pin insertion.
Figure 24:
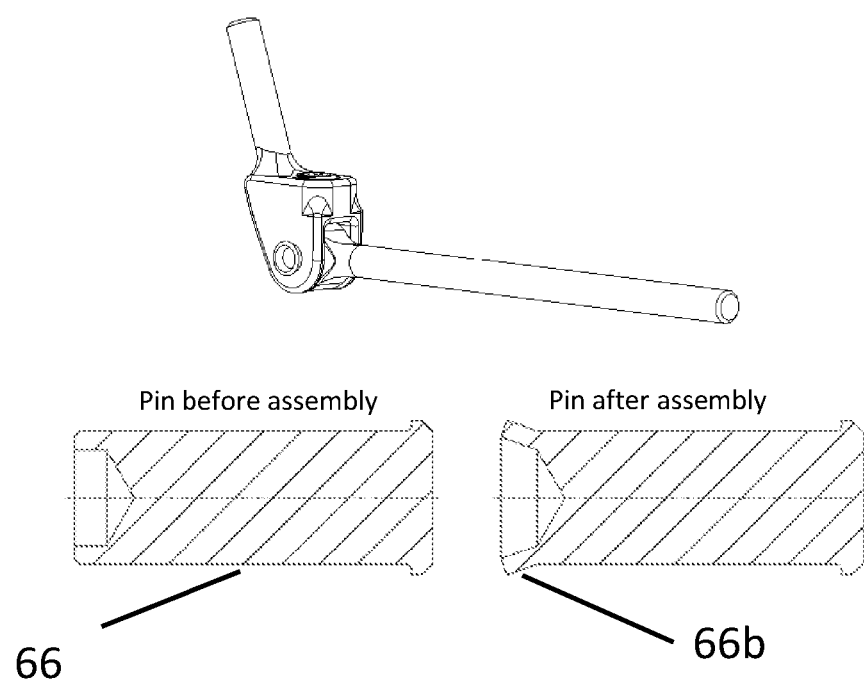
FIG. 24 is a depiction of the hinged plate assembly showing completion of pin insertion.
Figure 25:
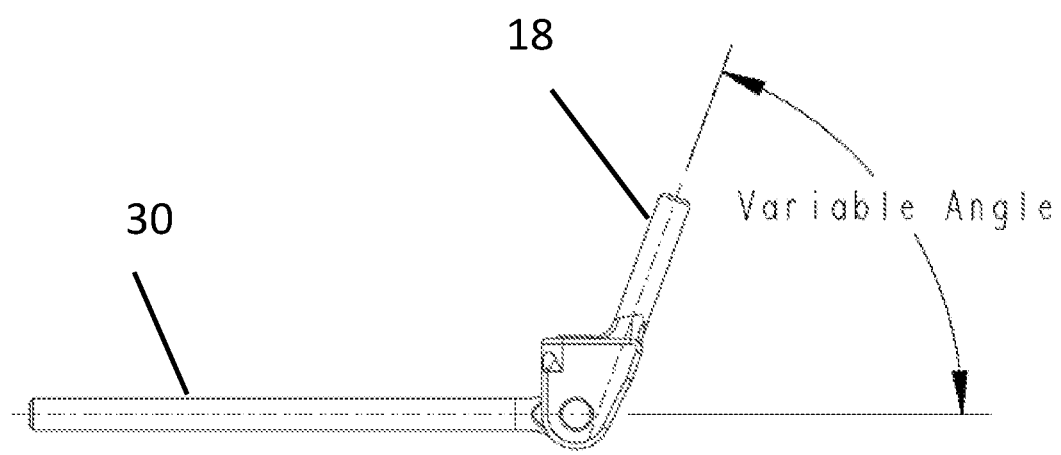
FIG. 25 is a depiction of the hinged plate assembly showing a range of angular rotation prior to locking the assembly in place.

FIGS. 21-25 are depictions of the hinged rod assembly 14 of the present invention. As apparent from the depictions, the hinged rod assembly 14 has 1) a female-type adapter having a housing 34 shown integrally connected to rod 18 (attachable to occipital plate 12 as shown in FIGS. 1) and 2) a male-type adapter in the form of a cylindrical end 62 having through hole 64. The male-type adapter is also shown integrally connected to rod 30 which extends down the vertebra. A pin 66 is inserted through holes in housing 34 and through a hole 64 of the cylindrical end of the male-type adapter 62. When not constrained, the cylindrical end 62 and the housing 34 can rotate about the axis defined by pin 66, thereby adjusting the angle between rods 18 and 30. A set screw 32 screws into female threads in housing 34 and binds the cylindrical end of the male-type adapter from rotation. As illustrated in FIGS. 23 and 24, pin 66 (prior to insertion) has on flared end 66a preventing it from sliding completely through the housing 34. After pin insertion, another flared end 66b is formed to prevent pin 66 from coming out of the housing. FIG. 25 illustrates the range of angular adjustment which in one embodiment can vary from 0 to 98 degrees, although other ranges of angular rotation are possible. As shown in FIG. 25, rod 18 and rod 30 can be angularly separated by an angle of rotation ranging from 82-180 degrees. Other angular ranges of separation are possible.

The occipital plate 12 can be composed of any applicable biocompatible material either currently known or developed in the future. It can also be constructed by means known in the art such as but not limited to machining, molding, and die pressing/extrusion. Likewise, the rods and the hinged rod assembly 14 can be formed by means known in the art such as but not limited to machining, molding, and die pressing/extrusion.

In this invention, the occipital plate and hinged rod assembly of this invention can be made of any material appropriate for human implantation and having the mechanical properties sufficient to be utilized for the intended purpose of spinal, including various metals such as cobalt chrome, stainless steel or titanium including its alloys, various plastics including those which are bio-absorbable, and various ceramics or combination sufficient for the intended purpose. In one embodiment, the implant is made of medical grade PEEK (polyetheretherketone). Further, the occipital plates of this invention may be made of a solid material, a mesh-like material, or a partially porous material and can be treated or coated with chemical substances such as bone, morphogenic proteins, hydroxyapatite in any of its forms, and osteogenic proteins, to make them biologically compatible.

This invention is also not limited to the methods by which the components of the occipital plate and hinged rod assembly are made. The individual components can be machined from solid stock pieces. Molding can be used to make the individual components. In this case, machining to final dimensions may or may not be in order. The surfaces once properly dimensioned can be coated with a variety of biocompatible coatings and/or surface treatments. Various coatings include for example calcium phosphate ceramics, such as tricalcium phosphate (TCP) and hydroxyapatite (HA), and hydroxyapatite (a naturally occurring material in bone). Moreover, If the implant is not made of bone, surfaces of the implant that contact bone may be treated to promote fusion of the implant to the bone. Treatment may include, but is not limited to, applying a hydroxyapatite coating on contact surfaces, spraying a titanium plasma on contact surfaces, and/or texturing the contact surfaces by scoring, peening, implanting particles in the surfaces, or otherwise roughening the surfaces of the implant.

In one embodiment of the invention, the holes and interconnecting openings described above in the occipital plate and in the hinged rod assembly can be machined into the body portion. In one embodiment of the invention, the holes and interconnecting openings in the occipital plate described above can be pressed into or formed with an uncured mold of the body portion after which the uncured mold is cured.

In some embodiments, any of the components of the occipital plate and hinged rod assembly described above (such as the insertion tool) can be used with additional implants and instruments. In some embodiments, the occipital plate and hinged rod assembly can be used with stabilization members, such as plates, screws, and rods.

This invention is also not limited to the shapes and designs noted above.

Figure 26:
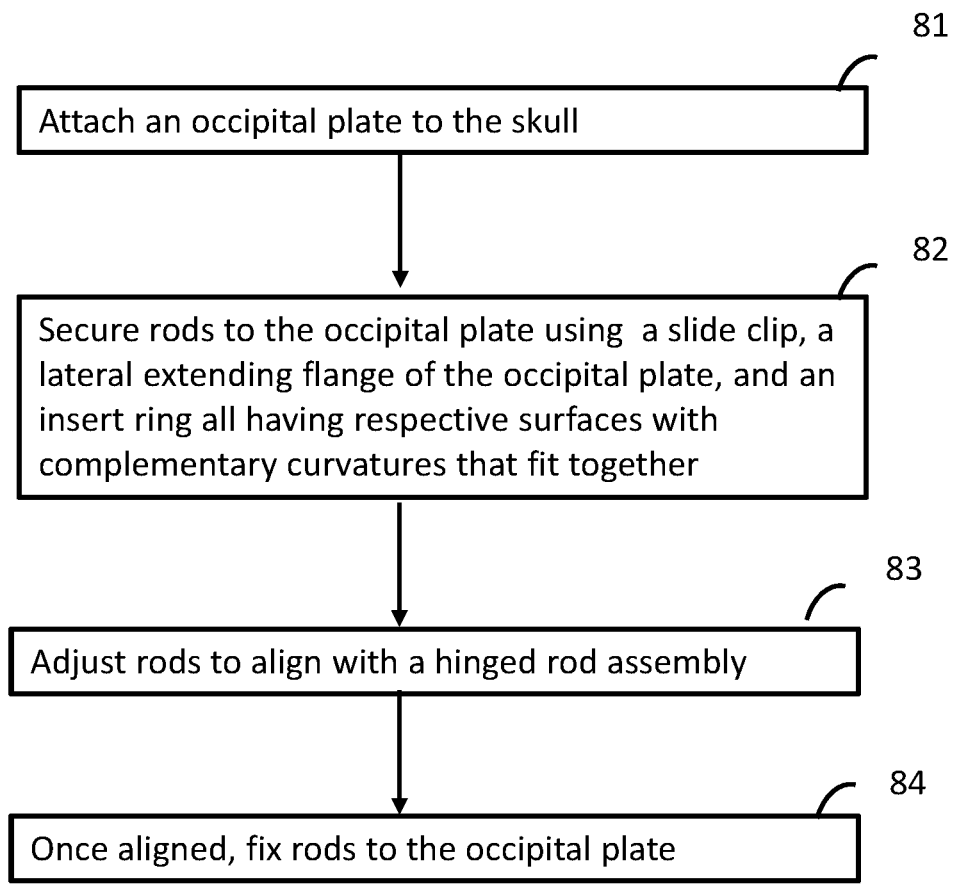
FIG. 26 is a flow diagram explaining a method of the present invention.

FIG. 26 is a flow diagram explaining one method of the present invention for immobilizing a patient's skull relative to the vertebra nearby the skull.

At 81, an occipital plate is attached to the skull. At 82, rods are secured to the occipital plate using a tulip connector which is connected to the occipital plate by a slide clip disposed underneath the occipital plate and an insert ring above the occipital plate with the slide clip, a laterally-extending flange of the occipital plate, and the insert ring having complementary curvatures which fit together.

At 83, the rods are adjusted (for example with a lateral displacement and lateral angular rotation) to align with a hinged rod assembly.

At 84, once aligned, the rods are fixed relative to the occipital plate by a screw threading into the tulip connection which pushes the rods onto the insert ring with the rod pushing the insert ring against the top surface of the occipital plate, thereby compressing the assembly of the tulip post connector, the slide clip, the laterally-extending section, and the insert ring together.

Generalized Statements of the Invention:

The following numbered statements describe generalized aspects or embodiments of the invention and are provided for illustrative purposes.

Statement 1. A bone attachment plate (such as an occipital plate) comprising:

a screw-attachment section having through holes for securing the occipital plate to a bone (such as the skull), a laterally-extending section connected to the screw-attachment section having at least one slot extending in a lateral direction, a tulip connector disposed in the at least one slot and comprising side walls which extend above the laterally-extending section, a slide clip disposed underneath the laterally-extending section and engaging a base of the tulip connector, and an insert ring encompassing the side walls of the tulip connector which extend above the laterally-extending section, wherein the laterally-extending section, the tulip connector, the slide clip, and the insert ring have respective surfaces with complementary curvatures that fit together.

Statement 2. The plate of statement 1, wherein the complementary curvatures all have the same radius of curvature.

Statement 3. The plate of statement 2, wherein, before the tulip connector is fixed to the laterally-extending section, the tulip connector is rotatable along the radius of curvature of the laterally-extending section.

Statement 4. The plate of statement 2, wherein, before the tulip connector is fixed to the laterally-extending section, the tulip connector is translatable in the at least one slot of the laterally-extending section Statement 5. The plate of statement 2, wherein, before the tulip connector is fixed to the laterally-extending section, the tulip connector is rotatable about an axis normal to the laterally-extending section and is rotatable in a plane normal to the laterally-extending section.

Statement 6. The plate of statement 1, wherein the laterally-extending section, and the insert ring all have the same radius of curvature, and the slide clip has a smaller radius of curvature.

Statement 7. The plate of statement 1, wherein the tulip connector comprises a sidewall section connected to the sidewalls, a flat on the sidewall section, a groove adjacent the flat section, and a base adjacent the groove.

Statement 8. The plate of statement 7, wherein the slide clip comprises a) a slot having an opening for accepting the groove of the tulip connector and b) a pocket at a longitudinal end of the slot for accepting the base of the tulip connector upon the tulip connector being raised normal to the laterally-extending section.

Statement 9. The plate of statement 8, wherein, once the tulip connector is raised normal to the laterally-extending section and the base is seated in the pocket of the slide clip, pins are inserted through the insert ring to engage the flat of the tulip connector.

Statement 10. The plate of statement 1, further comprising a screw configured to screw into threads on the sidewalls of the tulip connector in order to fix a rod in place relative to the laterally extending section.

Statement 11. A hinged rod assembly comprising: a female-type adapter having a housing integrally connected to a first rod, a male-type adapter integrally connected to a second rod, a pin inserted through a) a pair of aligned holes in the housing of the female-type adapter and b) through a hole in a cylindrical end of the male-type adapter, and a set screw which screws into female threads in the housing of the female-type adapter and binds the cylindrical end of the male-type adapter from rotation.

Statement 12. The assembly of statement 11, wherein the first rod is integrally formed with the housing of the female-type adapter.

Statement 13. The assembly of statement 11, wherein the second rod is integrally formed with the cylindrical housing of the male-type adapter.

Statement 14. The assembly of statement 11, wherein the pin comprises opposed flared ends securing the pin in the housing.

Statement 15. The assembly of statement 11, wherein the set screw is aligned in a plane normal to the pin.

Statement 16. The assembly of statement 11, wherein, once the set screw engages the cylindrical end of the male-type adapter, the first rod and the second rod are fixed and angularly separated by an angle of rotation ranging up to 180 degrees, or from 20-180 degrees, or from 40-180 degrees, or from 50-180 degrees, or from 60-180 degrees or from 70-180 degrees, or from 80-180 degrees other intermediate ranges.

Statement 17. The assembly of statement 11, wherein the housing has spaced apart arms, each arm having one of the aligned holes therein, and the arms are separated by a distance accommodating a width of the cylindrical end.

Statement 18. An occipital plate and hinged rod assembly comprising:
the occipital plate of any of the statements 1-10;
the hinged rod assembly of any of the statements 11-17.

Statement 19. The occipital plate and hinged rod assembly of statement 18, wherein
a pair of occipital plate rods extend from the occipital plate to the hinged rod assembly, and a pair of spine attachment rods extend from the hinged rod assembly away from the occipital plate.

Statement 20. The occipital plate and hinged rod assembly of any of the statements 18-19, wherein the occipital plate rods are laterally fixed by the occipital plate from each other by a lateral distance, a lateral angle, and a rotated angle rotated out of a plane of the occipital plate.

Statement 21. The occipital plate and hinged rod assembly of any of the statements 18-20, wherein the pair of occipital plate rods and the pair of spine attachment rods are angularly fixed relative to each other by the hinged rod assembly.

Statement 22. A tulip connector for securing a rod to a bone plate having a curved lateral-extending section, comprising: side walls which extend above the laterally-extending section, a sidewall section connected to the sidewalls, a flat on the sidewall section, a groove adjacent the flat section, a base adjacent the groove, and a screw configured to screw into threads on the sidewalls of the tulip connector in order to fix a rod in place relative to the laterally extending section.

Statement 23. The connector of claim 22, wherein, before the tulip connector is fixed to the laterally-extending section, the tulip connector is rotatable along a radius of curvature of the laterally-extending section.

Statement 24. The connector of statement 22, wherein, before the tulip connector is fixed to the laterally-extending section, the tulip connector is translatable in a slot of the laterally-extending section Statement 25. The connector of statement 22, wherein, before the tulip connector is fixed to the laterally-extending section, the tulip connector is rotatable about an axis normal to the laterally-extending section and is rotatable in a plane normal to the laterally-extending section.

Statement 26. A method for immobilizing a patient's skull relative to the vertebra nearby the skull, comprising attaching an occipital plate of any of statements 1-10 to the skull, securing rods to the occipital plate using a tulip connector of any of statements 22-25 by a slide clip disposed underneath the occipital plate and an insert ring above the occipital plate with the slide clip, the laterally-extending flange of the occipital plate, and the insert ring having respective surfaces with complementary curvatures that fit together. In this method, the rods are adjusted (for example with a lateral displacement and a lateral angular rotation and a rotation about an axis of the laterally-extending flange) to align with a hinged rod assembly. In this method, once aligned, the rods are fixed relative to the occipital plate by a screw threading into the tulip connection which pushes the rods onto the insert ring thereby compressing the assembly of the tulip post connector, the slide clip, the laterally-extending section, and the insert ring together.

Numerous modifications and variations of the present invention are possible in light of the above teachings. It is therefore to be understood that within the scope of the appended claims, the invention may be practiced otherwise than as specifically described herein.

The invention claimed is:

1. An occipital plate comprising:
a screw-attachment section having through holes for securing the occipital plate to a skull;
a laterally-extending section connected to the screw-attachment section having at least one elongated slot extending in a lateral direction away from the screw-attachment section and along a longitudinal axis of the laterally-extending section;
a tulip connector disposed in the at least one slot and comprising side walls which extend above the laterally-extending section;
a slide clip disposed underneath the laterally-extending section and engaging a base of the tulip connector; and
an insert ring encompassing the side walls of the tulip connector which extend above the laterally-extending section,
wherein the laterally-extending section, the tulip connector, the slide clip, and the insert ring have respective surfaces with complementary curvatures that fit together, and
wherein the complementary curvatures are configured to permit rotation of the tulip connector about the longitudinal axis of the laterally-extending section.

2. The plate of claim 1, wherein the complementary curvatures all have the same radius of curvature.

3. The plate of claim 2, wherein, before the tulip connector is fixed to the laterally-extending section, the tulip connector is rotatable along the radius of curvature of the laterally-extending section.

4. The plate of claim 2, wherein, before the tulip connector is fixed to the laterally-extending section, the tulip connector is translatable in the at least one elongated slot of the laterally-extending section.

5. The plate of claim 2, wherein, before the tulip connector is fixed to the laterally-extending section, the tulip connector is rotatable about an axis normal to the laterally-extending section and is rotatable in a plane normal to the laterally-extending section.

6. The plate of claim 1, wherein the laterally-extending section, the tulip connector, and the insert ring all have the same radius of curvature, and the slide clip has a smaller radius of curvature.

7. The plate of claim 1, wherein the tulip connector comprises a sidewall section connected to the sidewalls, a flat on the sidewall section, a groove adjacent the flat, and a base adjacent the groove.

8. The plate of claim 7, wherein the slide clip comprises a) a slot having an opening for accepting the groove of the tulip connector and b) a pocket at a longitudinal end of the slot for accepting the base of the tulip connector upon the tulip connector being raised normal to the laterally-extending section.

9. The plate of claim 8, wherein, once the tulip connector is raised normal to the laterally-extending section and the base is seated in the pocket of the slide clip, pins are inserted through the insert ring to engage the flat of the tulip connector.

10. The plate of claim 1, further comprising a screw configured to screw into threads on the sidewalls of the tulip connector in order to fix a rod in place relative to the laterally-extending section.

11. An occipital plate and hinged rod assembly comprising:
an occipital plate having:

a screw-attachment section having through holes for securing the occipital plate to a skull;

a laterally-extending section connected to the screw-attachment section having at least one elongated slot extending in a lateral direction away from the screw-attachment section and along a longitudinal axis of the laterally-extending section;

a tulip connector disposed in the at least one slot and comprising side walls which extend above the laterally-extending section;

a slide clip disposed underneath the laterally-extending section and engaging a base of the tulip connector; and an insert ring encompassing the side walls of the tulip connector which extend above the laterally-extending section, wherein the laterally-extending section, the tulip connector, the slide clip, and the insert ring have respective surfaces with complementary curvatures that fit together, and wherein the complementary curvatures are configured to permit rotation of the tulip connector about the longitudinal axis of the laterally-extending section;

a hinged rod assembly;

a pair of occipital plate rods extending from the occipital plate to the hinged rod assembly; and a pair of spine attachment rods extending from the hinged rod assembly away from the occipital plate.

12. The occipital plate and hinged rod assembly of claim 11, wherein the occipital plate rods are laterally fixed by the occipital plate from each other by a lateral distance, a lateral angle, and a rotated angle rotated out of a plane of the occipital plate.

13. The occipital plate and hinged rod assembly of claim 11, wherein the pair of occipital plate rods and the pair of spine attachment rods are angularly fixed relative to each other by the hinged rod assembly.

* * * * *